(12) United States Patent
LoVetri et al.

(10) Patent No.: US 12,721,595 B2
(45) Date of Patent: Sep. 1, 2026

(54) INTEGRATED MICROWAVE-ULTRASOUND BREAST IMAGING SYSTEM

(71) Applicant: University of Manitoba, Winnipeg (CA)

(72) Inventors: Joe LoVetri, Winnipeg (CA); Hannah Claire Fogel, Winnipeg (CA); Mohammad Asefi, Grande Pointe (CA)

(73) Assignee: University of Manitoba, Winnipeg (CA)

( * ) Notice: Subject to any disclaimer, the term of this patent is extended or adjusted under 35 U.S.C. 154(b) by 237 days.

(21) Appl. No.: 18/182,611

(22) Filed: Mar. 13, 2023

(65) Prior Publication Data

US 2023/0309958 A1 Oct. 5, 2023

Related U.S. Application Data

(60) Provisional application No. 63/325,586, filed on Mar. 30, 2022.

(51) Int. Cl.

| | |
|---|---|
| ***A61B 8/00*** | (2006.01) |
| ***A61B 5/0507*** | (2021.01) |
| ***A61B 8/08*** | (2006.01) |

(52) U.S. Cl.

CPC .......... *A61B 8/4416* (2013.01); *A61B 8/0825* (2013.01); *A61B 8/406* (2013.01);

(Continued)

(58) Field of Classification Search

CPC ..... A61B 8/4416; A61B 8/0825; A61B 8/406; A61B 8/4209; A61B 8/4488;

(Continued)

(56) References Cited

U.S. PATENT DOCUMENTS

2004/0030227 A1* 2/2004 Littrup .................... A61N 7/02 600/300
2004/0082856 A1* 4/2004 Marmarelis .......... A61B 8/0825 600/437

(Continued)

FOREIGN PATENT DOCUMENTS

CN 102499713 B * 5/2013
JP 2016101288 A * 6/2016

OTHER PUBLICATIONS

N. Abdollahi, D. Kurrant, p. Mojabi, M. Omer, E. Fear and J. LoVetri, "Incorporation of Ultrasonic Prior Information for Improving Quantitative Microwave Imaging of Breast," in IEEE Journal on Multiscale and Multiphysics Computational Techniques, vol. 4, pp. 98-110, 2019 (Year: 2019).*

(Continued)

*Primary Examiner* — Serkan Akar
(74) *Attorney, Agent, or Firm* — Kyle R Satterthweite; Ryan W Dupuis; Ade & Company Inc.

(57) ABSTRACT

A novel, integrated dual-modal breast imaging system that requires minimal or no movement of the breast between scans. A static receptacle holds the breast or other target object still. An acoustic imaging fixture with acoustic transducers, and an electromagnetic imaging chamber with electromagnetic antennae, each perform imaging of the target object when occupying a respective working position of surrounding relationship to the receptacle, and at least one thereof is movable relative to said static receptacle into and out of the respective working position, without repositioning of the static receptacle. Acoustic imaging is performed, and prior information extracted from the sound-speed image is incorporated into the electromagnetic inversion algorithm, whereby low-resolution sound-speed reconstructions are (Continued)

used to improve tumour detection via electromagnetic imaging.

17 Claims, 7 Drawing Sheets

(52) U.S. Cl.
CPC .......... *A61B 8/4209* (2013.01); *A61B 8/4488* (2013.01); *A61B 8/5223* (2013.01); *A61B 5/0507* (2013.01)

(58) Field of Classification Search
CPC ... A61B 8/5223; A61B 5/0507; A61B 5/0536; A61B 8/08; A61B 8/587
See application file for complete search history.

(56) References Cited

U.S. PATENT DOCUMENTS

2012/0029358 A1* 2/2012 Lin ...................... A61B 8/0825
600/447
2013/0204136 A1* 8/2013 Duric .................. G01S 15/8993
600/448
2014/0235962 A1* 8/2014 Yu ........................ A61N 5/1049
600/424
2015/0119682 A1* 4/2015 Nagae .................. A61B 5/0091
600/407
2016/0153940 A1* 6/2016 Kandori ............. G01N 29/2406
73/632
2019/0246941 A1* 8/2019 Bannister ............. A61B 5/0035

OTHER PUBLICATIONS

K. Nemez, A. Baran, M. Asefi and J. LoVetri, "Modeling Error and Calibration Techniques for a Faceted Metallic Chamber for Magnetic Field Microwave Imaging, " in IEEE Transactions on Microwave Theory and Techniques, vol. 65, No. 11, pp. 4347-4356, Nov. 2017. (Year: 2017).*
Machine translation of CN-102499713-B.*
Machine translation of JP-2016101288-A.*
Solis-Nepote et al. "An air-operated bistatic system for breast microwave radar imaging: Pre-clinical validation." 2019 41st Annual International Conference of the IEEE Engineering in Medicine and Biology Society (EMBC). IEEE, 2019. (Year: 2019).*

* cited by examiner 10
12
22B
36
32
26
22A
26
32
30
36
24
36
40
46
20
16
42
38
A_L
44
A_C
44A
18
44
14

10
12
14
16
18
20
22A
22B
24
26
30
32
34
36
38
40
44
44A
46
Ac 10
12
14
16
18
22A
22B
24
30
32
36
40
44
44A
46
Ac 40
38
Ac
12
22B
36
22A
42
46
20
14
16
18
44
44A

A
A
12
22A
22B
24
26
30
34
36

INTEGRATED MICROWAVE-ULTRASOUND BREAST IMAGING SYSTEM

CROSS-REFERENCE TO RELATED APPLICATIONS

This application claims benefit under 35 U.S.C. 119(e) of U.S. Provisional Application No. 63/325,586, filed Mar. 30, 2022, the entirety of which is incorporated herein by reference.

FIELD OF THE INVENTION

The present invention relates generally to 3D imaging, and more particularly to 3D imaging of the human breast for medical screening and diagnostic purpose.

BACKGROUND

Breast cancer affects many women worldwide. When caught early is often treatable, but current screening and diagnostic tools have considerable drawbacks. X-ray mammography Requires painful compression of the breast while imaging, uses ionizing radiation, and has poor sensitivity in women with dense breasts, who are most at risk for breast cancer. In the alternative case of traditional sonography, early-stage cancers are often missed, and image quality notably depends on the skill of the clinician. Magnetic resonance imaging (MRI) is expensive, time-consuming to operate, and is characterized by poor specificity, leading to unnecessary further tests or treatment.

Wavefield imaging offers a promising solution to overcome such shortcomings of the conventional screening and diagnostic tools. Wavefield imaging can be used to create a 3D image of physical properties of an object of interest, given a limited amount of data collected by sensors placed outside the object. In the case of microwave imaging (MWI), antennas illuminate the target and collect electromagnetic field data, and the aim is to reconstruct complex-valued permittivity of the object of interest. In the case of ultrasound imaging (USI), the target object is surrounded by piezoelectric transducers, and the aim is to reconstruct acoustic speed and/or attenuation.

Breast imaging using microwaves has been studied for several decades. It is well accepted that MWI lacks the resolution required for early detection of breast tumours, although quantitative MWI does have better specificity than some other modalities. Achieving accurate quantitative images of the complex-valued permittivity of the breast and improving the resolution remains an active area of research. One approach to enhancing microwave image quality (accuracy and resolution) is to incorporate information obtained from a second, complementary imaging modality into the microwave (MW) inversion algorithm. The integration of multi-modal imaging data may be accomplished via joint inversion, where data from the two imaging modalities are inverted simultaneously, or sequential inversions, where information about the object of interest (OI) is extracted from the first modality and used as prior information in the second inversion. Several studies have looked at methods for extracting prior information, for use in MWI, from other imaging modalities as well as integrating this information into inversion algorithms.

Quantitative USI for the breast is also an active area of research in its own right. USI uses smaller wavelengths, allowing for higher resolution reconstructions, and Quantitative USI can also provide improved specificity compared to traditional modalities. Some clinical quantitative USI systems for breast imaging exist, but these are expensive and highly specialized.

Accordingly, there remains a need for a wavefield breast imaging solution that at least partially addressing the foregoing shortcomings of the prior art.

SUMMARY OF THE INVENTION

According to a first aspect of the invention, there is provided a multi-modal imaging system comprising:

a static receptacle for holding an imaging target in a static position therein;

an acoustic imaging fixture sized and shaped to accommodate said static receptacle within an interior space of said acoustic imaging fixture in a working position of said acoustic imaging fixture that encompasses multiple sides of said static receptacle, said acoustic imaging fixture comprising an array of acoustic transducers thereon that are positioned and operable to transmit and receive acoustic signals across said interior space in the presence of said static receptacle for acoustic imaging of said imaging target held therein; and an electromagnetic imaging chamber also sized and shaped to accommodate said static receptable within an internal chamber space of said electromagnetic imaging chamber in a working position of said electromagnetic imaging chamber, said electromagnetic imaging chamber comprising an array of electromagnetic antennae thereon that are positioned and operable to transmit and receive electromagnetic signals in said internal chamber space in the presence of said static receptacle for electromagnetic imaging of said imaging target held therein;

wherein at least one of either the acoustic imaging fixture or the electromagnetic imaging chamber is movable relative to said static receptacle into and out of the respective working position of encompassing relationship to the static receptacle.

According to a second aspect of the invention, there is provided a method of imaging of an imaging target, said method comprising:

receiving the imaging target in a static receptacle; and in either order, and with the imaging target remaining stationary in a static position inside the static receptable both during and between the following steps, (a) acquiring acoustical imaging data using an array of acoustic transducers arranged in a working state surrounding said static receptacle on multiple sides thereof to transmit and receive acoustical signals through the static receptacle and the imaging contained target therein; and (b) acquiring electromagnetic imaging data using an array of electromagnetic antennae arranged in a working state surrounding said static receptacle on multiple sides thereof and within an electromagnetic imaging chamber that encompasses said multiple sides of said electromagnetic imaging chamber.

BRIEF DESCRIPTION OF THE DRAWINGS

Preferred embodiments of the invention will now be described in conjunction with the accompanying drawings in which.

DETAILED DESCRIPTION

Figure 1:
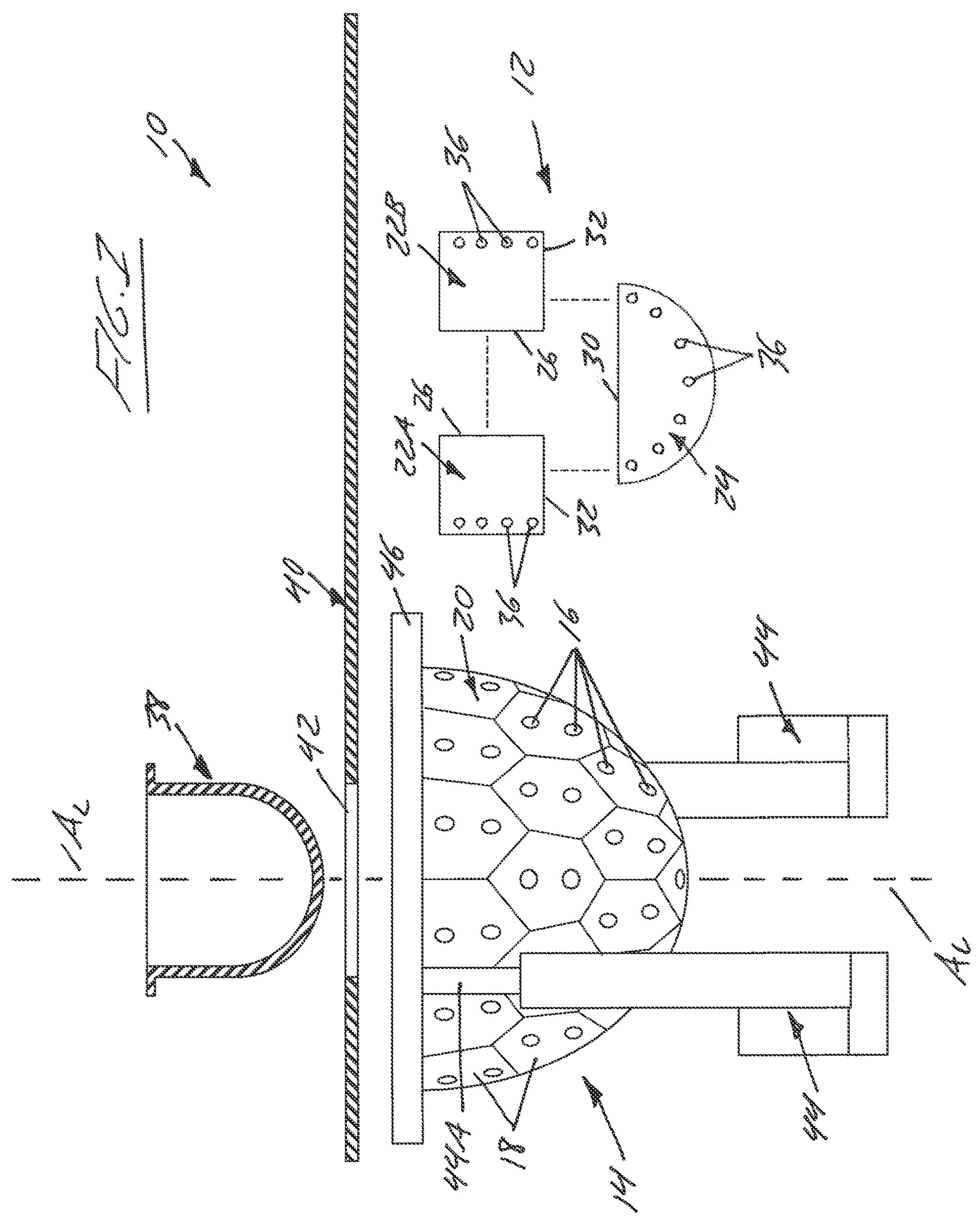
FIG. 1 is a partially exploded and partially cross-sectioned view of cooperative components of a novel dual-mode microwave-ultrasound imaging apparatus according to one preferred embodiment of the present invention.

Preferred embodiments of the present invention adopt the aforementioned sequential inversion approach to multi-modal imaging, where information about the object of interest (OI) is extracted from the first modality and used as prior information in the second inversion. More specifically, such embodiments utilize prior information, in the form of relatively low-resolution reconstructions derived from a relatively simple USI system that is combined with a known MWI system. In contrast, the other aforementioned approach, in which the MW and ultrasound (US) data are simultaneously inverted, generally requires that more extensive US data be obtained in order to match the resolution on the single reconstruction mesh. In some embodiments, as is the case of the prototyped embodiment, the inversion algorithm is the finite-element method contrast-source inversion (FEM-CSI) technique that allows prior information to be included as either an initial guess or as an inhomogeneous numerical background, as described in below cited references [16]-[19]. The US sound-speed reconstructions use a ray-based technique with a polynomial basis approximation, per below cited reference [20].

FIGS. 1 to 4 schematically illustrate a novel dual-mode microwave-ultrasound imaging apparatus 10 according to one preferred embodiment of the present invention, in which a removable US fixture 12 is combined with an MWI chamber 14. The MWI chamber 14 is an air-based flat-faceted quasi-resonant chamber, the details of which have been previously published in below cited references [15], [16], in view of which a full restatement of such details is not explicitly included herein. In brief, the MWI chamber is an opened topped chamber whose internal volume is of an approximately hemi-ellipsoidal shape, but whose internal surface is composed of flat facets, rather than a smoothly continuous surface of concave curvature. Magnetic field probe antennae, are installed in the faceted wall 20 of the chamber operable to transmit and receive electromagnetic signals within the chamber's internal space for the purpose of making S-parameter measurements. In FIGS. 1 to 5, the presence of such antennae is denoted by presence of probe mounting ports 16 in the faceted chamber wall 20 where such field probe antennae can be installed at selected facets, whereas the field probe antenna are labeled schematically at 16A in the block diagram of FIG. 6. In the prototyped embodiment, the MWI chamber 14 is characterized by forty-four facets 18, of which twenty-four facets have respective field probe antennae installed in the ports 16 of those facets. Full details of a working MW measurement system connectable to the field probe antennae of this this MWI chamber 14 to perform such measurements are incorporated herein by reference from below cited reference [15].

The US fixture 12 of the illustrated embodiment is a multi-piece assembly composed of two hollow semi-cylindrical pieces 22A, 22B plus a semi-spherical cap 24. The US fixture 12 is shown exploded in an unassembled state in FIGS. 1 to 3 and 5, and in an assembled working state in FIG. 4. Of the three US fixture components 22A, 22B, 24, the two semi-cylindrical pieces 22A, 22B mate together at their longitudinal edges 26 that lie axially of the semi-cylindrical shape of each piece, such that the two pieces 22A, 22B to cooperatively form an upright cylindrical wall 28 of the US fixture 12. The semi-spherical cap 24 has a circular top rim 30, which mates with the arcuate bottom ends 32 of the semi-cylindrical pieces 22A, 22B in the assembled state of the US fixture 12. The semi-cylindrical shape of each wall piece 22A, 22B of the US fixture 12 can be seen in the top view of FIG. 5, where the top end 34 of each piece can be seen to posses the aforementioned arcuate shape also possessed at the piece's bottom end 32. The three components 22A, 22B, 24 may be mechanically coupled together using any suitable interlocking features, latches or removable fasteners, and so, in the interest of illustrative simplicity, the components are 22A, 22B, 24 shown in simplified schematic form lacking such coupling details.

In the assembled state of the US fixture 12, the semi-spherical fixture cap 24 forms an internally concave, closed bottom end of the assembled US fixture 12, thus capping off the bottom end of the fixture's upright cylindrical wall 28. The assembled US fixture 12 houses an array of single-element piezoelectric transducers, schematically illustrated at 36, of which a respective subset of these transducers 36 is possessed by each of the three fixture components 22A, 22B, 24. In the prototyped embodiment, there are sixty-four piezoelectric transducers 36, arranged in a helical fashion around a central longitudinal axis of the assembled US fixture 12, though the transducers 36 are shown in simplified schematic form without accurate reproduction of such helical layout. In use of the inventive multi-modal imaging apparatus 10, the multi-piece US fixture 12 is easily taken apart to remove the fixture from the imaging target (e.g. human breast) after US data collection. An accompanying US data measurement system (schematically shown in FIG. 6) is operable to drive the transducers 22 with an arbitrary waveform.

Figure 2:
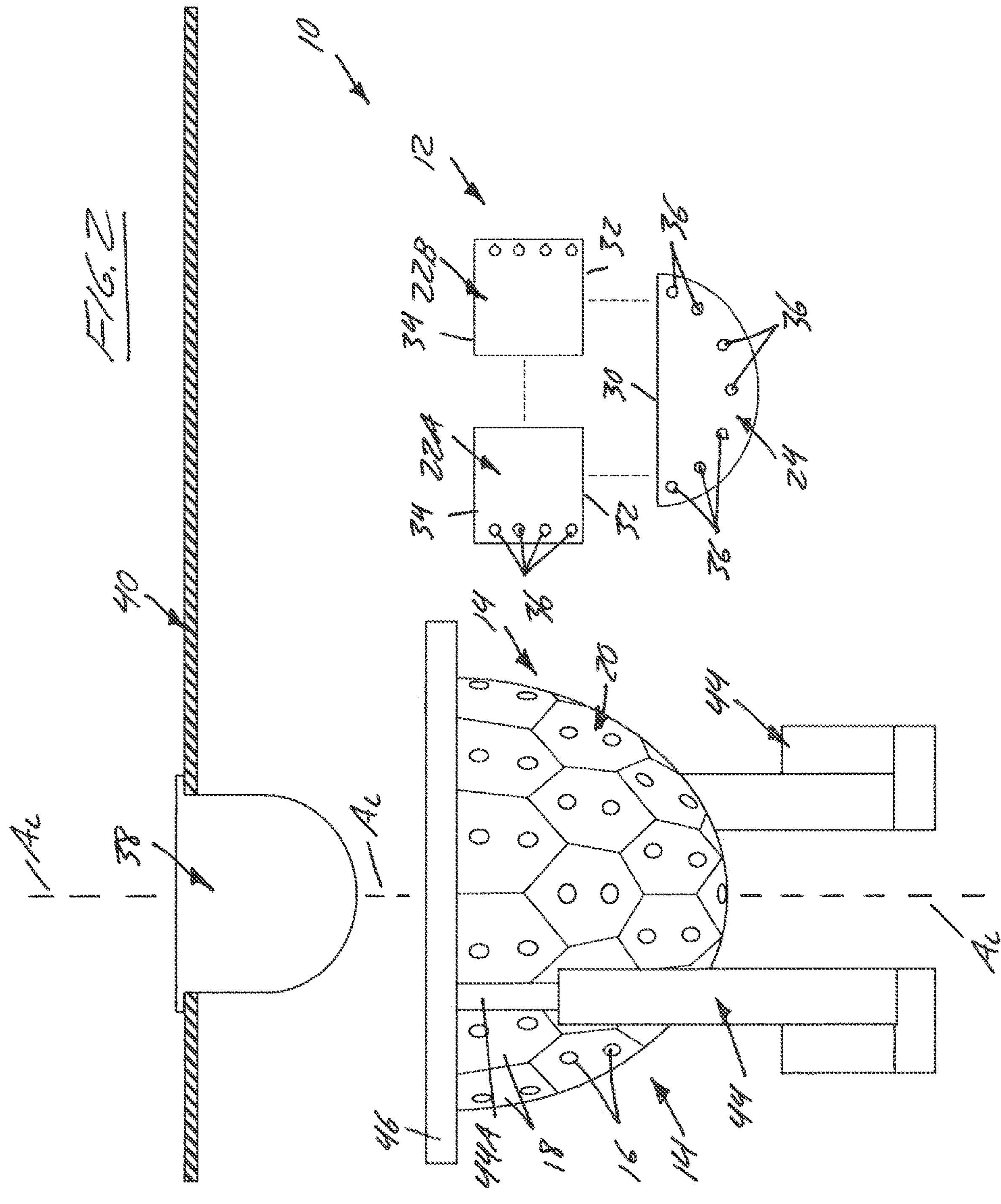
FIG. 2 illustrates the system of FIG. 1 in a prepared state ready for use, with a breast cup installed in a patient table to receive a breast of a patient laid prone atop the patient table.

The US fixture 12 is designed to fit snugly around a flexible breast-support cup 38, which is shown in cross-section and in exploded from its normally installed position in FIG. 1, but is shown un-sectioned in its installed position in FIG. 2. The breast support cup 38, or breast cup for short, serves as a static receptable for holding the breast in a known shape and static position during the imaging process, while also imposing minimal compression on the breast. When assembled around the breast cup 38, the US fixture 12 encompasses all sides of the breast cup 38 in a circumferential direction therearound, and also encompasses the closed bottom end of the breast cup 38, within the concave interior of the fixture's bottom cap 24. As a result, the acoustic transducers 36 that are helically arrayed around the interior of the US fixture 12, and operable to transmit and receive ultrasound signals across an interior space of the assembled US fixture 12, are in physical contact with the outside of the flexible breast cup 38, whereby the transducers and are thus operable to transmit those signals through the static breast cup 24 for ultrasound imaging of the breast held statically therein.

The breast cup 38 is installed in a patient table 40, or other comparable type of patient support, atop which a patient may lie in a prone position. The patient table 40 has a hole 42 therein that penetrates through the patient table 40 from a topside thereof to an opposing underside thereof. The breast cup 38 is installed at the hole 42 of the patient table 40, from which the installed breast cup 38 hangs down from the underside of the patient table. In use, the breast of a patient lying prone atop the table 40 is received within the breast cup 38 and through the hole 42 in the table.

The MWI chamber 14 resides beneath the patient table 40 in aligned relation to the breast cup 38 and the patient table hole 42 at which the breast cup 38 is installed. The MWI chamber 14 is movable relative to the patient table 40, and more particularly is movable relative thereto into and out of a position of surrounding working relation to the breast cup 38 for the purpose of imaging the patient breast received therein. In the illustrated embodiment, the MWI chamber 14 is linearly displaceable upwardly and downwardly on an upright longitudinal axis $A_L$ shared by the MWI chamber 14, breast cup 38 and patient table hole 42 by one or more linear actuators 44. In the illustrated example, the push rod 44A of each linear actuator 44 is attached to an out-turned flange 46 of the MWI chamber 14 of radially projecting relationship to the chamber wall 20, for example at a top end thereof. In this example, the actuator(s) 44 thus perform(s) direct lifting and lowering of the MWI chamber 14, but it will be appreciated that the linear actuator(s) 44 or other type of actuation means may alternatively perform lifting and lowering of the MWI chamber 14 via indirect connection thereto, for example by lifting and lowering a chamber support platform atop which the MWI chamber 14 is mounted.

Figure 3:
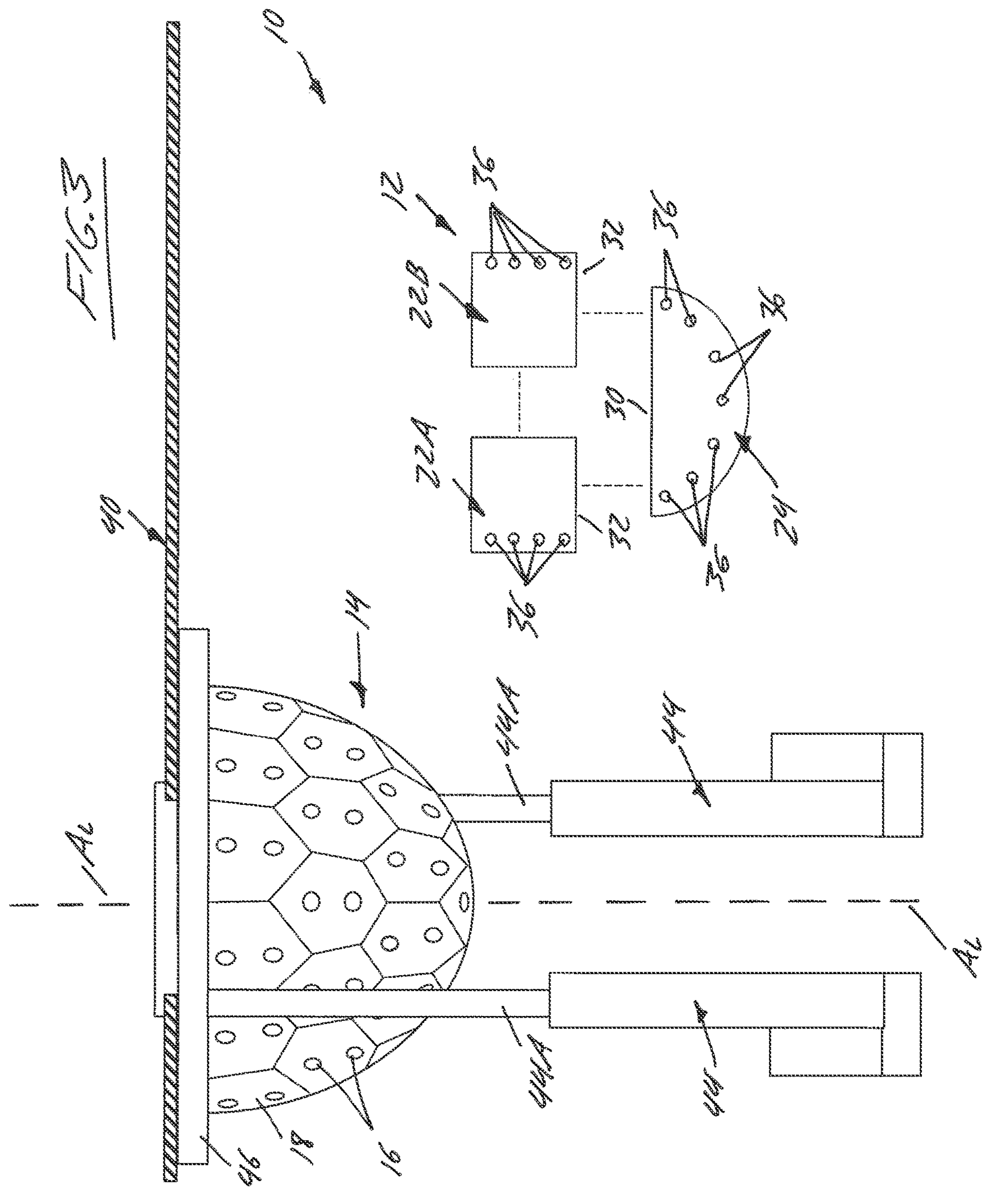
FIG. 3 illustrates the system of FIG. 1 in a first stage of use, where an MWI chamber has been lifted into a raised working position surrounding the breast cup to perform MW imaging of the patient breast.

FIG. 3 shows the actuator(s) 44 in an extended position that places the MWI chamber 14 in a raised working position surrounding the breast cup 38 in close or abutting relationship to the underside of the patient table 40 in order to take MW measurements of the patient breast inside the breast cup 38. During this MW measurement stage of the process, the removable US fixture 12 is left unassembled and absent from the breast cup 24 so that the MW measurements of the breast can be taken of the cup-held imaging target (the patient breast), without interference by the US fixture 12. In contrast, FIG. 4 shows the actuator(s) 44 a retracted position in which the MWI chamber 14 resides in a lowered non-working position withdrawn from around the breast cup 38 and residing at a spaced elevation therebelow, and thus further away from the patient table 40.

Figure 4:
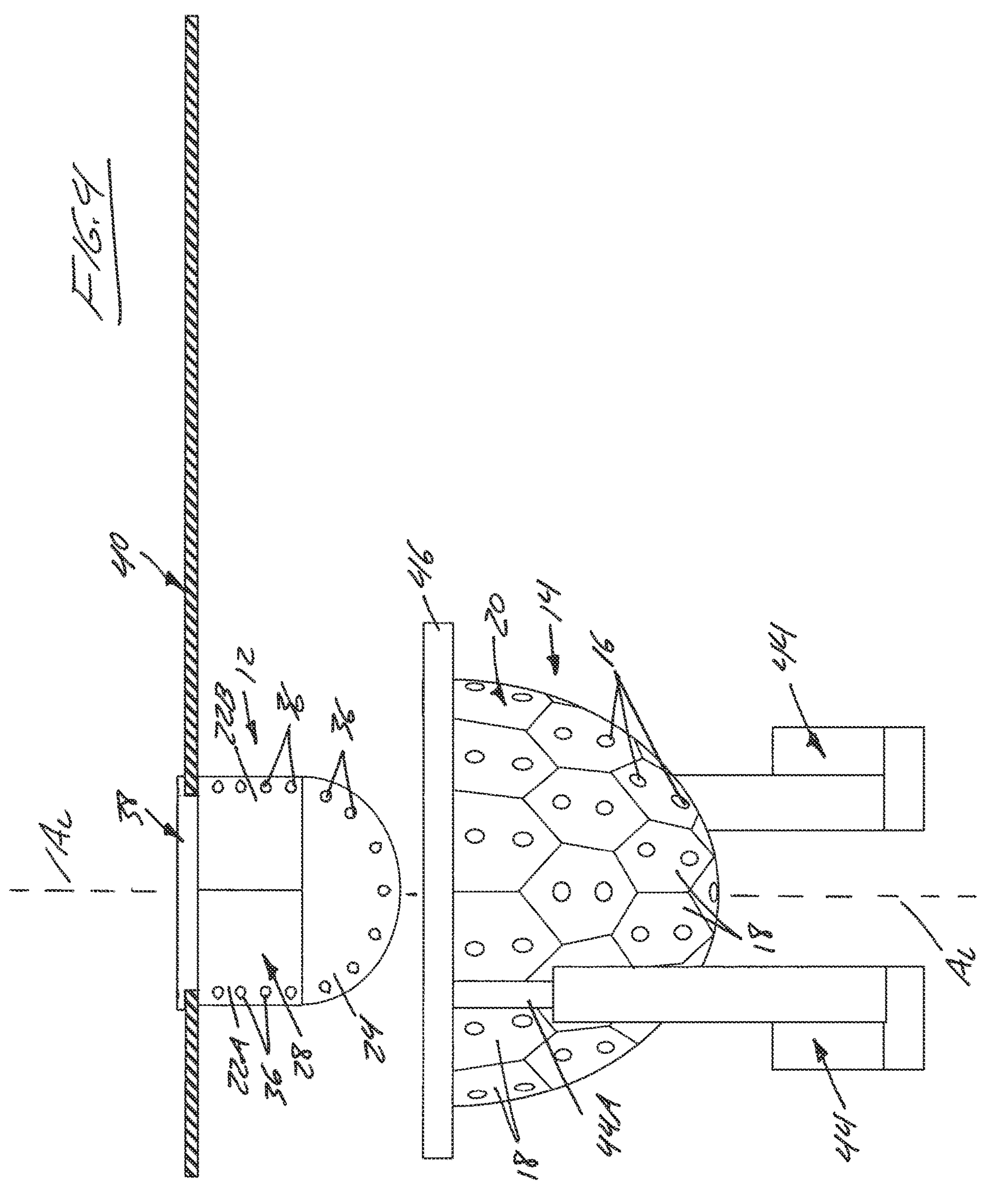
FIG. 4 illustrates the system of FIG. 3 in a second stage of use, where the MWI chamber has been lowered to a non-working position withdrawn from the breast cup, and a US fixture has been placed in a working state surrounding the breast cup to perform US imaging of the patient breast.

With the MWI chamber 14 retracted in FIG. 4 to expose the breast cup 38, the components 22A, 22B, 24 of the US fixture 12 can be assembled or otherwise placed into a working state of mated together relation to one another and surrounding relation to the breast cup 38 at the underside of the patient table 40. Once so placed or assembled, the US fixture 12 is held secure in this working state position, for example via a clamped or locked attachment to the underside of the table 40, whereupon the US measurements are then be taken. After completion of the US measurements, the components 22A, 22B, 24 of the US fixture 12 can be separated from one another and withdrawn from around the breast cup 38, so as to no longer reside in working relation thereto, thus rendering the overall multi-modal imaging apparatus 10 ready for repetition of the forgoing procedure, for example on another breast of the same patient, or a breast of a subsequent new patient.

Figure 4A:
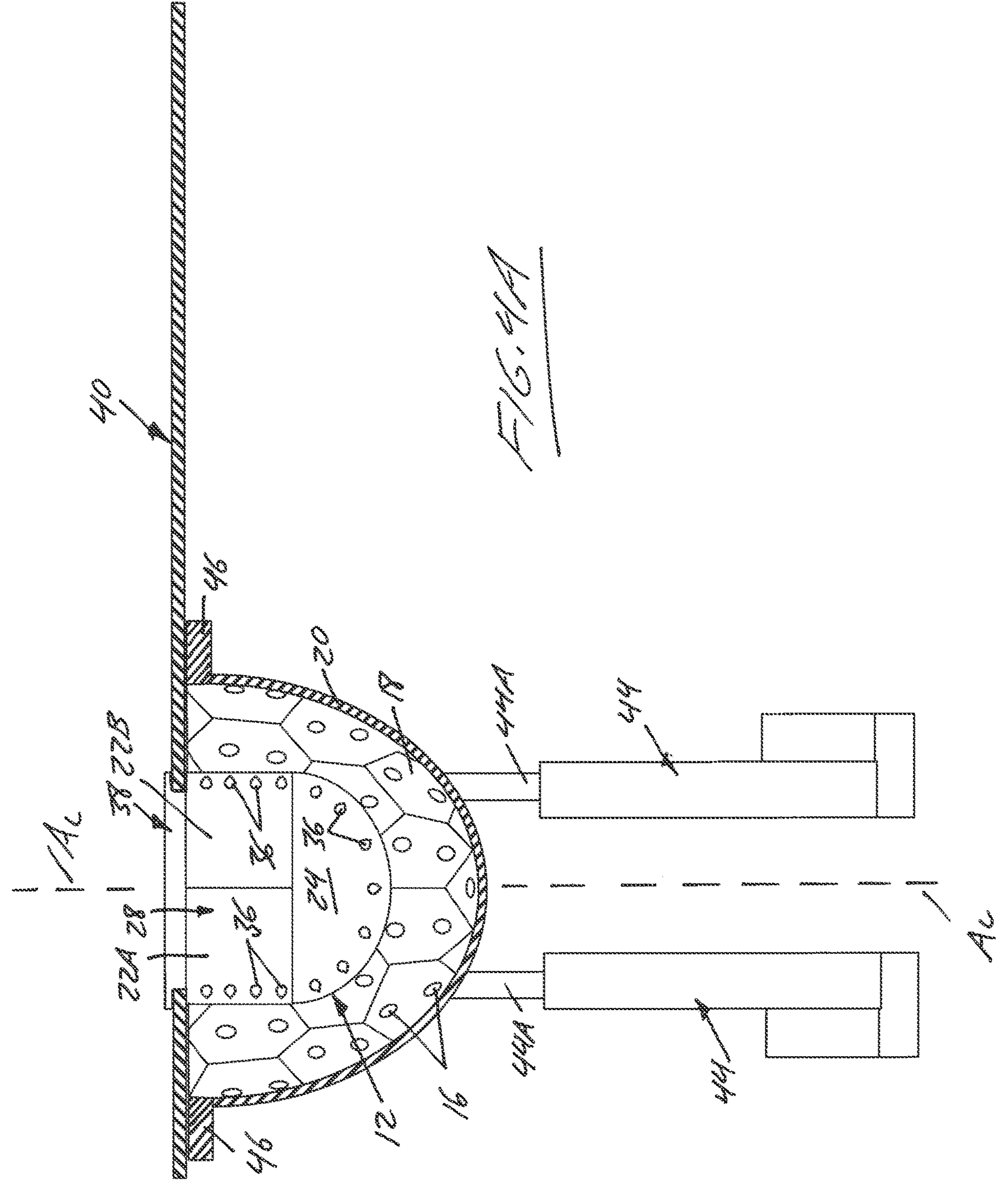
FIG. 4A illustrates a variant of FIG. 4, where after placement of the US fixture around the breast cup, the MWI chamber once again is lifted to its raised position, so as to surround both the breast cup and the US fixture during the US imaging process.
Figures 5, 5A:
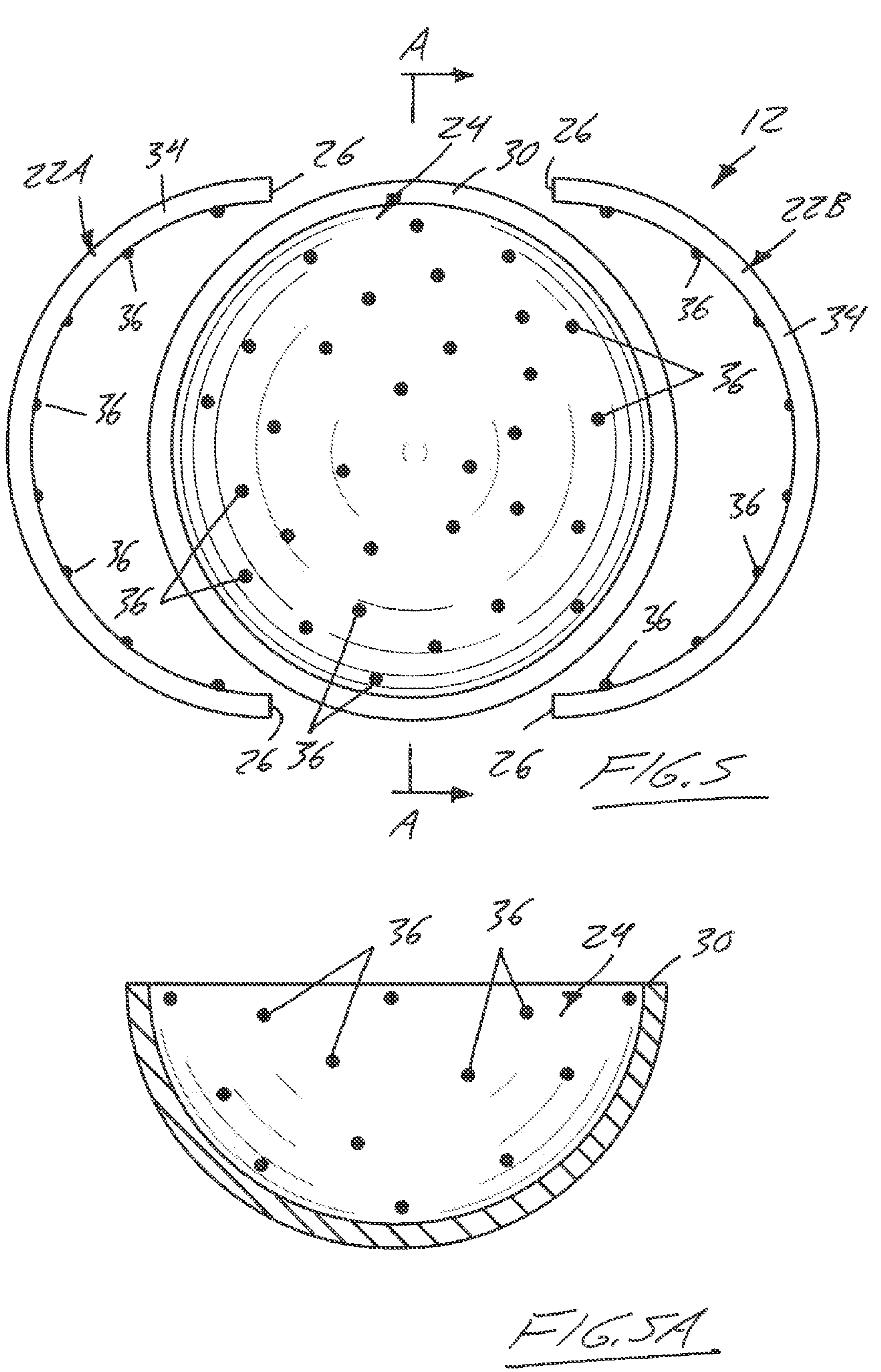
FIG. 5 is a top plan view of the US fixture in the same disassembled non-working state in which it is shown in side elevation in FIGS. 1 to 3.
FIG. 5A is a cross-sectional view of a bottom cap of the US fixture of FIG. 5, as viewed along line A-A thereof.

Throughout the US and MW measurement procedures, and throughout the transition of the MWI chamber 14 and US fixture 12 into and out of their respective working positions surrounding the breast cup 38, the table-supported breast cup 38, and the patient's breast received therein, remain statically positioned. With reference to FIG. 4A, where the wall 20 of the MWI chamber 14 and the rod 44A of the left actuator 44 have been cut away for illustrative purpose, it can be seen the assembled US fixture 12 of the illustrated embodiment is small enough for nested receipt thereof inside the larger MWI chamber 14, whereby the MWI chamber 14 can optionally occupy its raised position while the US fixture is in its working state around the breast cup 38. In such embodiments, it may therefore be possible to take the US measurements with the US fixture 12 in its working position immediately surrounding the breast cup 38, and the MWI chamber 14 also in its raised working position, in which instance surrounds the US fixture 12.

While the forgoing paragraphs describe working placement of the MWI chamber 14 and taking of the MW measurements as occurring prior to the working placement of the US fixture 12 and taking of the US measurements, it will be appreciated that the order may be reversed. While the illustrated embodiment features machine powered lifting and lowering of the MWI chamber, for example using linear actuators or other powered lifting means, and lacks any powered means of placing and removing the US fixture components 22A, 22B, 24 into and out of their working relationship to the breast cup 38, it will be appreciated that other degrees or combinations of powered actuation and/or human performed placement of the MWI chamber 14 and US fixture 12 may alternatively be employed. For example, fixture-manipulating actuators may be attached the underside of the patient table 40, or otherwise supported therebeneath, for the purpose of laterally sliding the two semi-cylindrical pieces 22A, 22B together from initially withdrawn positions that are situated radially far enough from the breast cup 38 to reside outside the MWI chamber 14 when raised. The bottom cap 24 of the US fixture 12 may likewise be placeable by one or more actuators into mating relationship with the bottoms 32 of the mated semi-cylindrical pieces 22A, 22B from an initially withdrawn position of likewise non-obstructive relationship to the raising and lowering of the MWI chamber 14, for example being laterally slid into aligned relation under the bottom ends of the semi-cylindrical pieces 22A, 22B by a respective fixture actuator.

Figure 6:
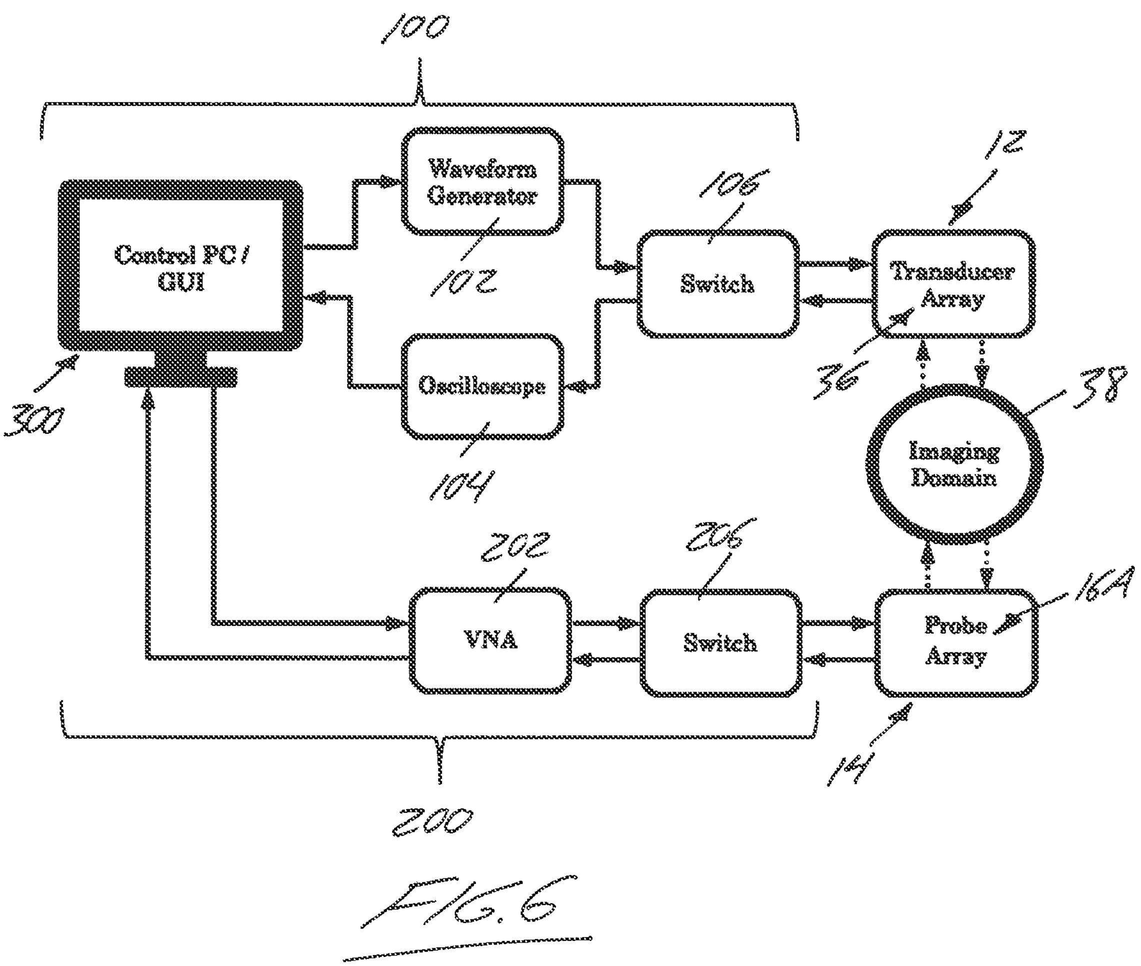
FIG. 6 is a schematic block diagram an overall dual-mode microwave-ultrasound imaging system employing the apparatus of FIGS. 1 to 5.

A notable feature of the dual-modal imaging apparatus 10 detailed above is that the US fixture 12 is easily installed and removed, by coupling and decoupling of component pieces of the US fixture into and out of snugly surrounding relation to a statically supported breast cap, thereby denoting an ability to obtain scattered-field data from the MW and US measurement systems that, as schematically shown in FIG. 6, are respectively connected to the MWI chamber's field probe antennae and the US fixture's transducers 36, without re-positioning the breast between the taking of the MW and US measurements, and regardless of which order they are taken. Another advantageous aspect is simplified registration between the two modalities due to the use of an air-based MWI chamber (with no immersion medium), that does not introduce breast deformity due to buoyancy. The use of a breast-support cup 38 within the MWI chamber denotes a combination that can be easily incorporated into the aforementioned FEM-CSI inversion model. The 3D printed prototype of the US fixture 12 demonstrated the achievability of a small, lightweight US fixture that is inexpensive to manufacture.

FIG. 6 schematically illustrates a fully operational dual-mode microwave-ultrasound imaging system, in which the illustrated apparatus of FIGS. 1 to 5 is combined with the aforementioned US measurement system 100 and MW measurement system 200. The US measurement system 100 includes an arbitrary waveform generator 102 and an oscilloscope 104, both connected to a computer 300, and a custom-built switch 106 for a routing a transmitted signal from the waveform generator 102 to a computer-specified one of the transducers 36 of the US fixture 12, and associated routing received measurement signals from all the other transducers to corresponding channels of the oscilloscope 104. Control software, saved in non-transitory computer readable memory of the computer(s) 300 for execution of such software of one or more processors of the computer(s), includes a US measurement algorithm that coordinates such excitation of a specified transducer by the waveform generator, and associated data storage of the received measurement signals from the other transducers, on a repeated basis, until completion of a full measurement cycle in which each transducer has served as the transmitting transducer, thereby collecting and storing a full US measurement data set. The US measurement algorithm is triggerable, for example, by selection of a US measurement start command in a graphical user interface (GUI) displayed on the computer 300 by the control software, once the US fixture 12 is placed in its working position surrounding the breast cup 38. After collection of the full US measurement data set, the control software executes one or more US inversion algorithms to reconstruct the sound-speed and acoustic attenuation inside the imaging domain.

In a non-limiting example reflective of the prototyped embodiment of the present invention, the arbitrary waveform generator may be comprised of four PC-based waveform generator cards (e.g. Signatec PXDAC4800), each with four channels, and a pulsed sinusoid truncated after five periods may be used to drive the US transducers at their observed resonant frequency of 1.4 MHz. The oscilloscope may be, for example, a 32-channel digital oscilloscope, composed of four PC-based oscilloscope cards (e.g. GaGe Octopus 8387 CompuScope digitizer boards), each with 8 channels. The US transducers 36 (e.g. from Sonometrics Corporation, London, Canada) may be single-element piezoelectric transducers, whose elements consists of a cylindrical lead zirconate titanate (PZT-5H) crystal, connected to a twisted pair of wires and dipped in epoxy to provide better coupling to the background material, assumed to be water or similar. The twisted pair may be surrounded by a ground shield and encased inside a waterproof coating. The usable bandwidth of the transducers may be approximately 1.0-1.8 MHz.

In place of the waveform generator 102 and oscilloscope 104 found in the US measurement system, the MW measurement system 200 instead features a vector network analyzer 202, whose ports are connected to the MW field probe antennae 16A of the MWI chamber 14 via another switch 206. Via execution of an MW measurement algorithm of the control software on the computer 300, e.g. via selection of an MW measurement start command in the GUI once the MWI chamber 14 is in the working position (with the US fixture 12 absent from the breast cup 38), the field probe antennae 16A illuminate the target object (the patient breast inside the breast cup 38) with electromagnetic energy in the microwave frequency range, typically in the range of 0.3-9 GHz for biomedical applications, and field data are collected from all antenna positions in the MWI chamber, and stored by the computer 300.

The MWI chamber may feature forty-four facets, approximating a hemi-ellipsoidal shape, with S-parameter measurements being made using the magnetic field probes (half-loop antennas) installed on 24 of the facets. The antennas may be connected via coaxial cables to a 24-port vector network analyzer (VNA), for example comprised of four 6-port Keysight PXIe VNA modules (Keysight Technologies, Santa Rosa, CA, USA). The air-based MWI chamber 14 simplifies registration of the target object (patient breast) between the two imaging systems, as the variable buoyancy of breasts can lead to unpredictability of the exact position and shape of the breast in a fluid-filled chamber.

Before an MW inversion algorithm of the control software 300 is executed, an intermediate mapping step is performed, in which the reconstructed values of acoustic speed obtained from the US inversion algorithm are mapped to complex permittivity values, different mapping techniques may be used, for example segmented mapping, linear mapping or tissue-range mapping. After such mapping has been performed, the MW inversion algorithm is then executed to reconstruct the complex-valued permittivity, related to the dielectric constant and loss, of tissues within the imaging domain. This MW inversion algorithm takes as input both the stored MW measurement data set as well as the mapped permittivity values derived from the US inversion algorithm, the latter of which is the "prior information" that links the USI and MWI modes of the inventive dual-mode system. The US-derived prior information may be used by the MW inversion algorithm in different ways, for example as an "initial guess" or as an "inhomogeneous numerical background". The resultant output from the MW inversion algorithm is a final image, which shows the complex-valued permittivity inside the target object (breast), and can be displayed to the operator in the GUI. While the illustrated embodiment of FIG. 6 shows a singular control computer 300, it will be appreciated that other embodiments may employ a plurality of computers, among which the control software and its various algorithms may be distributed in any manner.

In the prototype, the patient table 40 was substituted for a smaller support rested atop the out-turned flange 46 at the top of the MWI chamber 14, by which the breast cup 38, and the assembled US fixture 12, when present during the US measurement stage, could be suspended within the MWI chamber 14. In this prototype apparatus, the MWI chamber 14, instead of being linearly displaced relative to the resting support, remained static, with reliance being made on manual lifting of the resting support (and attached breast cup 28 and US fixture 12) from off the flanged top of the MWI chamber 14 to enable installation and removal of the US fixture 12. Testing was conducted using a breast phantom consisting of four distinct tissue regions: skin, fat, fibroglandular and tumour, with the tumour embedded inside the fibroglandular region. For each tissue type, both the complex-valued permittivity and acoustic sound-speed of the phantom material were designed to approximate the values of real breast tissue. The skin region was a 2 mm thick, 10 cm diameter cylindrical shell with a hemi-spherical cap. The shell was made from a graphite-urethane mixture, and its total height was 9.64 cm. Construction details are available in below cited reference [21]. The shell had a measured relative permittivity of 11-j1.2 at 1 GHz. The fat region consisted of canola oil, having a measured relative permittivity of 2.9-j0.23 at 1 GHz and sound-speed of 1463 m/s at 1.4 MHz, the center frequency of the US transducers 36. The fibroglandular and tumour regions were composed of gelatin-based mixtures. The recipes were derived from the acoustic breast phantom described in below cited reference [22], modified so that the phantoms also exhibit dielectric properties representative of the respective breast tissue. The fibroglandular region was composed of water, gelatin, agar, glycerin, and n-propanol, whereas the tumour consisted of water, gelatin, agar, glycerin and table salt. The liquid mixtures were heated just until boiling, and left to set inside custom molds. The fibroglandular region was asymmetric, as depicted in Applicant's related provisional application, incorporated herein by reference. The tumour is ellipsoidal in shape, with diameters of 2 and 2.5 cm. The relative permittivities of the fibroglandular and tumour regions at 1 GHz were 41-j8.4 and 71-j19, respectively, and measured sound-speeds are 1595 and 1587 m/s, respectively. Note that the tumour and fibroglandular sound-speeds are approximately the same, considering the accuracy of the present USI system. This is contrary to the fact that the sound-speed of tumour tissue is known to be higher than that of fibroglandular tissue. Photographs of the phantom components are shown in Applicant's related provisional application, in which the relative complex permittivities of the fat, fibroglandular and tumour-mimicking materials are also plotted as a function of frequency.

The US data was collected first, with the US fixture 12 holding the US transducers 36 in positions making direct contact with the skin of the phantom, which doubled as the breast support cup in the experimental setup. Good contact was ensured by using ultrasonic coupling gel, which is preferably also used on the exterior of the breast support cup in preferred working embodiments of the present invention. The US data consists of time-domain transmission pulse waveforms from which time-of-flight (TOF) between each Tx/Rx pair is extracted. For the results presented herein, a pulsed sinusoid having a frequency of 1.4 MHz truncated after five periods was used. The TOF data was used within a ray-based reconstruction algorithm that utilizes whole-domain polynomial basis functions of variable order to approximate the sound-speed within the breast. The whole breast was used as the imaging domain. Details of the reconstruction algorithm are provided in below cited reference [20]. Once the US time-domain data was acquired, the US fixture 12 was carefully removed, and frequency-domain MW data was acquired at several frequencies between 1-2 GHz.

To invert the MW data and reconstruct an image of the complex-valued permittivity within the breast phantom, the FEM-CSI algorithm was used. Although there are several methods that can be used to integrate the prior (in this case ultrasound) information into FEM-CSI reconstructions, two have been prevalent in past work: a) using it as an initial guess, or b) introducing it as a numerical background that changes the contrast being sought. The latter technique was implemented in a previous MWI breast phantom study, published in below cited reference [16]. Both require that the reconstructed sound-speed values be converted to complex-valued permittivity. There are various ways of performing this mapping, which is the subject of ongoing study. Below are provided initial results of using the prior information as both an initial guess, and as an inhomogeneous background.

US reconstruction was obtained using 5th order basis functions, resulting in creation of permittivity maps, which are shown in Applicant's related provisional application. The conversion from sound-speed to permittivity was accomplished using a tissue-range mapping technique similar to that published in below cited reference [23]. For an MW-only case, single-frequency results at 1.0 and 1.3 GHz were obtained. For these cases, perfect prior information (both geometric and permittivity) of the skin and fat regions were incorporated into the inversion algorithm as a numerical inhomogeneous background. No prior information related to the fibroglandular region was assumed. These MW reconstructions (without US-derived prior, but with perfect knowledge of the skin and fat) were created, and are also shown in Applicant's related provisional application. The imaging domain was limited to the fat region. These results were quite poor given that no fibroglandular prior was included, as was expected from the study performed in below cited reference [16]. In that prior work, tumour detection was shown to be quite good with the inclusion of perfect fibroglandular prior. Of course, the purpose in the testing context of the present invention was to determine just how "perfect" the fibroglandular prior must be, that is, using imperfect prior obtained from the coarse US reconstructions.

The dual-mode inversion results using the US-derived initial guess are shown in Applicant's related provisional application, along with those using the US-derived background. It is noted that the scales of the colour bars in the permittivity reconstructions of the provisional figures are not all the same: the MW-only reconstructions achieved a peak-value that was considerably lower than the true value. From the results, it was clear that the MWI produces some structure within the US fibroglandular prior that was supplied. When the prior was incorporated as an inhomogeneous numerical background, there seemed to be more irregular structures and, in addition, it was found that the permittivity values saturated to the maximum value that was imposed as a constraint in the FEM-CSI inversion. On the other hand, when using the prior as an initial guess, the permittivity values within the fibroglandular region still did not reach the measured values of the tumour. So, it was concluded that there was "undershooting" in the initial guess case, and "overshooting" in the inhomogeneous background case. From the obtained images, it was unclear which of the two techniques provides better tumour detection, but it was reasonable to say that either provides better detection compared to when no prior is provided.

At the time of testing, a systematic tumour detection algorithm, such as one of the techniques applied in below cited reference [16], had not yet been implemented for the dual-mode results. Applicant's related provisional application includes image examples of tumour detection using a simple thresholding technique for one set of parameters that produced better reconstructions; that is, choosing over the reconstructions obtained with different inversion parameters: inversion frequency and the order of the US basis functions used. Before the images were thresholded, artefacts at the top of the image were manually removed. Such artefacts were observed to be typical in the sound-speed reconstructions, and thus could be safely removed when present. In the thresholded images found in Applicant's related provisional application, the threshold value was set to 96% of the peak value in the reconstruction.

The test results were clear: that the use of the US prior information, as either an initial guess or as a background, has resulted in an improved detectability of the tumour. The results presented demonstrated the ability of the novel, dual-mode microwave-ultrasound system to reconstruct quantitative images using a preliminary attempt at a realistic dual-mode breast phantom.

Since various modifications can be made in my invention as herein above described, and many apparently widely different embodiments of same made, it is intended that all matter contained in the accompanying specification shall be interpreted as illustrative only and not in a limiting sense.

REFERENCES

The following references, and any and all other references cited or mentioned elsewhere herein, are incorporated herein by reference in their entirety.

[1] J.-C. Bolomey, "Crossed viewpoints on microwave-based imaging for medical diagnosis: From genesis to earliest clinical outcomes," in The World of Applied Electromagnetics. Springer, 2018, pp. 369-414.

[2] B. M. Moloney, D. O'Loughlin, S. Abd Elwahab, and M. J. Kerin, "Breast cancer detection—a synopsis of conventional modalities and the potential role of microwave imaging," Diagnostics, vol. 10, no. 2, p. 103, 2020.

[3] P. Mojabi and J. LoVetri, "Experimental evaluation of composite tissue-type ultrasound and microwave imaging," IEEE Journal on Multiscale and Multiphysics Computational Techniques, vol. 4, pp. 119-132, 2019.

[4] D. O'Loughlin, M. O'Halloran, B. M. Moloney, M. Glavin, E. Jones, and M. A. Elahi, "Microwave breast imaging: Clinical advances and remaining challenges," IEEE Transactions on Biomedical Engineering, vol. 65, no. 11, pp. 2580-2590, 2018.

[5] X. Song, M. Li, F. Yang, S. Xu, and A. Abubakar, "Study on joint inversion algorithm of acoustic and electromagnetic data in biomedical imaging," IEEE Journal on Multiscale and Multiphysics Computational Techniques, vol. 4, pp. 2-11, 2019.

[6] Y. Qin, T. Rodet, M. Lambert, and D. Lesselier, "Joint inversion of electromagnetic and acoustic data with edge-preserving regularization for breast imaging," IEEE Transactions on Computational Imaging, vol. 7, pp. 349-360, 2021.

[7] G. Boverman, C. E. Davis, S. D. Geimer, and P. M. Meaney, "Image registration for microwave tomography of the breast using priors from nonsimultaneous previous magnetic resonance images," IEEE journal of electromagnetics, RF and microwaves in medicine and biology, vol. 2, no. 1, pp. 2-9, 2017.

[8] D. Kurrant and E. Fear, "Regional estimation of the dielectric properties of inhomogeneous objects using near-field reflection data," Inverse Problems, vol. 28, no. 7, p. 075001, 2012.

[9] M. Omer, P. Mojabi, D. Kurrant, J. LoVetri, and E. Fear, "Proof-of-concept of the incorporation of ultrasound-derived structural information into microwave radar imaging," IEEE Journal on Multiscale and Multiphysics Computational Techniques, vol. 3, pp. 129-139, 2018.

[10] N. Abdollahi, D. Kurrant, P. Mojabi, M. Omer, E. Fear, and J. LoVetri, "Incorporation of ultrasonic prior information for improving quantitative microwave imaging of breast," IEEE Journal on Multiscale and Multiphysics Computational Techniques, vol. 4, pp. 98-110, 2019.

[11] P. Mojabi, N. Abdollahi, M. Omer, D. Kurrant, I. Jeffrey, E. Fear, and J. LoVetri, "Tissue-type imaging for ultrasound-prior microwave inversion," in 2018 18th International Symposium on Antenna Technology and Applied Electromagnetics (ANTEM), 2018, pp. 1-3.

[12] N. Duric, P. Littrup, L. Poulo, A. Babkin, R. Pevzner, E. Holsapple, O. Rama, and C. Glide, "Detection of breast cancer with ultrasound tomography: First results with the computed ultrasound risk evaluation (cure) prototype," Medical physics, vol. 34, no. 2, pp. 773-785, 2007.

[13] N. Duric, P. Littrup, and C. Kuzmiak, "Breast ultrasound tomography," Breast Imaging, vol. 6, 2018.

[14] N. Duric, M. Sak, S. Fan, R. M. Pfeiffer, P. J. Littrup, M. S. Simon, D. H. Gorski, H. Ali, K. S. Purrington, R. F. Brem et al., "Using whole breast ultrasound tomography to improve breast cancer risk assessment: a novel risk factor based on the quantitative tissue property of sound speed," Journal of clinical medicine, vol. 9, no. 2, p. 367, 2020.

[15] K. Nemez, A. Baran, M. Asefi, and J. LoVetri, "Modeing error and calibration techniques for a faceted metallic chamber for magnetic field microwave imaging," IEEE Transactions on Microwave Theory and Techniques, vol. 65, no. 11, pp. 4347-4356, 2017.

[16] M. Asefi, A. Baran, and J. LoVetri, "An experimental phantom study for air-based quasi-resonant microwave breast imaging," IEEE Transactions on Microwave Theory and Techniques, vol. 67, no. 9, pp. 3946-3954, 2019.

[17] I. J. Amer Zakaria, J. LoVetri, and A. Zakaria, "Full-vectorial parallel finite-element contrast source inversion method," Progress In Electromagnetics Research, vol. 142, pp. 463-483, 2013.

[18] D. Kurrant, A. Baran, J. LoVetri, and E. Fear, "Integrating prior information into microwave tomography part 1: Impact of detail on image quality," Medical physics, vol. 44, no. 12, pp. 6461-6481, 2017.

[19] D. Kurrant, E. Fear, A. Baran, and J. LoVetri, "Integrating prior information into microwave tomography part 2: Impact of errors in prior information on microwave tomography image quality," Medical physics, vol. 44, no. 12, pp. 6482-6503, 2017.

[20] M. Hughson, "Quantitative transmission tomography for non-destructive imaging of stored grain and biological tissue," Master's thesis, University of Manitoba, 2021.

[21] J. D. Garrett, "Average dielectric property analysis of non-uniform structures: Tissue phantom development, ultra-wideband transmission measurements, and signal processing techniques," Master's thesis, University of Calgary, 2014.

[22] L. Medina-Valdés, M. Pérez-Liva, J. Camacho, J. Udías, J. Herraiz, and N. González-Salido, "Multimodal ultrasound imaging for breast cancer detection," Physics Procedia, vol. 63, pp. 134-140, 2015.

[23] C. Kaye, I. Jeffrey, and J. LoVetri, "Improvement of multi-frequency microwave breast imaging through frequency cycling and tissue-dependent mapping," IEEE Transactions on Antennas and Propagation, vol. 67, no. 11, pp. 7087-7096, 2019.

The invention claimed is:

1. A multi-modal imaging system comprising:

a patient-receiving structure configured to host a patient in a static body position during and throughout a multimodal imaging process;

a receptacle secured and maintained in a statically held state at a fixed location supported proximate to the patient-receiving structure, and configured to receive and statically hold a body part of the patient in a static position inside said receptacle at said fixed location;

an acoustic imaging fixture sized and shaped to accommodate said receptacle within an interior space of said acoustic imaging fixture in a working position of said acoustic imaging fixture that is configured to both physically engage with and encompass multiple sides of said receptacle, wherein said acoustic imaging fixture further comprises an array of acoustic transducers configured to be positioned in physical contact, in said working position of the acoustic imaging fixture, with the receptacle or the body part received therein, and which acoustic transducers are operable in said working position to transmit and receive acoustic signals through the body part for acoustic imaging thereof; and an electromagnetic imaging chamber also sized and shaped to accommodate said receptacle within an internal space of said electromagnetic imaging chamber in a working position of said electromagnetic imaging chamber that encompasses the receptacle at the fixed location proximate to the patient-receiving structure, said electromagnetic imaging chamber comprising an array of electromagnetic antennae that are positioned statically thereon at positions distributed around the internal space and are configured to transmit and receive electromagnetic signals in said internal space in the presence of said receptacle for electromagnetic imaging of said body part held statically therein;

a chamber mover operable to move the electromagnetic imaging chamber, relative to both the patient-receiving structure and the fixed location of the receptacle, between the working position that encompasses the receptacle at the fixed location proximate to the patient-receiving structure, and a non-working position withdrawn away from the fixed location of the receptacle to a spaced distance therefrom to enable placement of the acoustic imaging fixture into its working position with the electromagnetic imaging chamber withdrawn;

wherein:

the receptacle is supported independently of the electromagnetic imaging chamber and the chamber mover so as to remain static at the fixed location throughout any movement of the electromagnetic imaging chamber by the chamber mover;

the acoustic imaging fixture is configured for selective disengagement from the receptacle in non-disruptive relation to the statically held state, and the fixed location of, both the receptacle and the body part received therein, and said acoustic imaging fixture is further configured for withdrawal away from the receptacle, when disengaged therefrom, to a withdrawn state of external relationship to an electromagnetic imaging space that is instead independently encompassed by the electromagnetic imaging chamber when in the working position thereof; the chamber mover is operable to move the electromagnetic imaging chamber into the working position thereof in a state of the system in which the acoustic imaging fixture is in the withdrawn state thereof, such that the internal space of the electromagnetic imaging chamber, when moved into the respective working position thereof by the chamber mover, is unoccupied by the ultrasonic fixture, thereby enabling unobstructed electromagnetic imaging of the body part inside the receptacle; and the acoustic imaging fixture and the electromagnetic imaging chamber are configured to occupy their respective working positions at different acoustic and electromagnetic imaging stages of the multi-modal imaging process, among which the electromagnetic imaging stage is characterized by the working position of the electromagnetic imaging chamber and the withdrawn state of the acoustic imaging fixture, and the acoustic imaging stage is characterized by the working position of at least the acoustic imaging fixture, and the receptacle is configured to maintain the body part in a statically held condition inside the receptacle at the fixed location throughout a totality of the multi-modal imaging process, including the acoustic imaging stage, the electromagnetic imaging stage, and all transitional stages therebetween during which the acoustic imaging fixture and the electromagnetic imaging chamber are transitioned into and out of their respective working positions, whereby optimal image registration between electromagnetic and acoustic imaging data respectively collected during the electromagnetic and acoustic imaging stages is optimally enabled by the statically held condition of the body part throughout the totality of the multi-modal imaging process.

2. The system of claim 1 wherein the acoustic imaging fixture is a multi-piece fixture that, in addition to said acoustic transducers, comprises a plurality of fixture pieces that are selectively matable together around the receptacle in achievement of the respective working position of the acoustic imaging fixture, and selectively extractable from one another to disengage from the receptacle.

3. The system of claim 2, wherein said plurality of fixture pieces each host a respective subset of the acoustic transducers.

4. The system of claim 2, wherein said plurality of fixture pieces comprise curved wall pieces mateable together to cooperatively form a cylinder that encompasses the receptacle in a circumferential direction therearound.

5. The system of claim 4, wherein said plurality of fixture pieces further comprise a cup piece mateable with bottom ends of the curved wall pieces to close a bottom end of the cylinder and encompass an underside of the receptacle.

6. The system of claim 1 wherein said acoustic transducers are ultrasound transducers.

7. The system of claim 1 wherein said electromagnetic antennae are microwave antennae.

8. The system of claim 1 wherein said receptacle is flexible.

9. The system of claim 1 wherein said receptacle comprises an open cup for receiving the body part through an open top thereof.

10. The system of claim 1 wherein the receptacle hangs from an underside of the patient-receiving structure for hanging receipt therein of the body part of the patient when laying atop said patient-receiving structure.

11. The system of claim 10 wherein the chamber mover comprises at least one linear actuator for raising and lowering of the electromagnetic imaging chamber.

12. The system of claim 1 wherein the acoustic imaging fixture is smaller than the electromagnetic imaging chamber.

13. The system of claim 12 wherein, in addition to the electromagnetic imaging chamber being movable into the respective working position thereof with the acoustic imaging fixture disengaged and withdrawn from the receptacle, the electromagnetic imaging chamber is also movable into surrounding relationship to the working position of the acoustic imaging fixture.

14. The system of claim 1 wherein the acoustic imaging fixture is smaller than the electromagnetic imaging chamber and, the respective working position of the acoustic imaging fixture, is surroundable by said electromagnetic imaging chamber during said acoustic imaging stage.

15. The system of claim 1 wherein the electromagnetic imaging chamber is an air-based electromagnetic imaging chamber void of any immersion liquid.

16. The system of claim 1 wherein the acoustic transducers are distributed both axially along and circumferentially around the acoustic fixture.

17. The system of claim 1 wherein the acoustic transducers are distributed helically around the acoustic fixture.

* * * * *